(12) United States Patent
Kasuga et al.

(10) Patent No.: US 9,539,365 B2
(45) Date of Patent: *Jan. 10, 2017

(54) FIBER WADDING FOR FILLING BONE DEFECTS

(71) Applicants:Orthorebirth Co. Ltd., Kanagawa (JP); Nagoya Institute of Technology, Aichi (JP)

(72) Inventors: Toshihiro Kasuga, Aichi-ken (JP); Akiko Obata, Aichi (JP); Kie Fujikura, Aichi (JP); Yoshio Ota, Kanagawa (JP); Xianfeng Yao, Kanagawa (JP)

(73) Assignees: Orthorebirth Co. Ltd., Kanagawa (JP); Nagoya Institute of Technology, Nagoya-shi, Aichi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/495,649

(22) Filed: Sep. 24, 2014

(65) Prior Publication Data

US 2015/0079147 A1 Mar. 19, 2015

Related U.S. Application Data

(63) Continuation of application No. 13/350,569, filed on Jan. 13, 2012, now Pat. No. 8,853,298, which is a continuation-in-part of application No. 12/707,302, filed on Feb. 17, 2010, now abandoned.

(30) Foreign Application Priority Data

Jul. 10, 2009 (JP) ............................. 2009-163320
Feb. 3, 2011 (JP) ............................. 2011-021790

(51) Int. Cl.
*A61F 2/28* (2006.01)
*C08K 9/02* (2006.01)
(Continued)

(52) U.S. Cl.
CPC ............ *A61L 27/446* (2013.01); *A61F 2/28* (2013.01); *A61K 9/70* (2013.01); *A61K 31/755* (2013.01);
(Continued)

(58) Field of Classification Search
USPC ........................................ 523/115, 204, 216
See application file for complete search history.

(56) References Cited

U.S. PATENT DOCUMENTS 5,676,699 A  10/1997  Gogolewski et al.
6,641,773 B2  11/2003  Kleinmeyer et al.
(Continued)

FOREIGN PATENT DOCUMENTS

JP  H06-319794 A  11/1994
JP  H07-265337 A  10/1995
(Continued)

OTHER PUBLICATIONS

Hotta et al., "Preparation of poly(lactic acid) microfiber mats containing calcium carbonate particles by an electrospinning method", 11th Symposium on Ceramics in Medicine, Biology and Biomimetics, Dec. 7, 2007, pp. 15, Japan.*
(Continued)

*Primary Examiner* — Tae H Yoon
(74) *Attorney, Agent, or Firm* — Osha Liang LLP

(57) ABSTRACT

A fiber wadding for filling bone defects having a flocculent three-dimensional structure is disclosed. The fiber wadding includes a plurality of fibers that contain a biodegradable resin as a principal component and a siloxane. Outside diameter of the plurality of fibers of the wadding is from about 0.05 µm to about 30 µm. Bulk density of the fiber wadding is about 0.005-0.3 g/cm$^3$.

12 Claims, 9 Drawing Sheets

(51) Int. Cl.
| | |
|---|---|
| A61L 27/32 | (2006.01) |
| A61L 27/44 | (2006.01) |
| A61L 27/18 | (2006.01) |
| A61L 27/26 | (2006.01) |
| A61K 9/70 | (2006.01) |
| A61K 31/755 | (2006.01) |
| A61K 31/80 | (2006.01) |
| A61K 33/10 | (2006.01) |
| A61L 24/02 | (2006.01) |
| A61L 24/04 | (2006.01) |
| A61L 27/54 | (2006.01) |
| A61L 27/58 | (2006.01) |
| A61F 2/30 | (2006.01) |
| A61F 2/44 | (2006.01) |

(52) U.S. Cl.
CPC .............. *A61K 31/80* (2013.01); *A61K 33/10* (2013.01); *A61L 24/02* (2013.01); *A61L 24/046* (2013.01); *A61L 27/18* (2013.01); *A61L 27/26* (2013.01); *A61L 27/32* (2013.01); *A61L 27/54* (2013.01); *A61L 27/58* (2013.01); *A61F 2/3094* (2013.01); *A61F 2002/4495* (2013.01); *A61L 2430/02* (2013.01); *Y10T 442/2033* (2015.04)

(56) References Cited

U.S. PATENT DOCUMENTS

| | | | | |
|---|---|---|---|---|
| 7,374,774 | B2 * | 5/2008 | Bowlin | A61F 2/08 424/423 |
| 8,853,298 | B2 * | 10/2014 | Kasuga | A61F 2/28 442/63 |
| 2002/0177903 | A1 | 11/2002 | Geistlich et al. | |
| 2004/0101959 | A1 | 5/2004 | Marko et al. | |
| 2005/0287239 | A1 | 12/2005 | Joo et al. | |
| 2008/0296808 | A1 | 12/2008 | Joo et al. | |
| 2010/0303881 | A1 | 12/2010 | Hoke et al. | |
| 2012/0058090 | A1 * | 3/2012 | Lelkes | A61L 15/32 424/93.21 |
| 2012/0135448 | A1 | 5/2012 | Parker et al. | |

FOREIGN PATENT DOCUMENTS

| | | |
|---|---|---|
| JP | 2001-294673 A | 10/2001 |
| JP | 2001-519210 A | 10/2001 |
| JP | 2002-085547 A | 3/2002 |
| JP | 2003-517326 A | 5/2003 |
| JP | 2004-105754 A | 4/2004 |
| JP | 2006-187303 A | 7/2006 |
| JP | 2008-100878 A | 5/2008 |
| JP | 2009-061109 A | 3/2009 |
| WO | 99/37240 A2 | 7/1999 |
| WO | 2008/099140 A2 | 8/2008 |
| WO | 99/19005 A1 | 4/2010 |

OTHER PUBLICATIONS

Obata et al., PLA/Vaterite Composite Microfiber Membranes for GBR, IUMRS-ICA 2008, Dec. 9-13, 2008, 1 page, Japan.*
Obata et al., "Preparation of poly(lactic acid)/silicon-doped calcium carbonate composite fibrous mats by electrospinning". ISAEM-2008, Nagoya, Nov. 18-21, 2008, 1 page, Japan.*
Office Action issued Feb. 23, 2016, in related U.S. Appl. No. 14/728,544 (17 pages).
Tsuru, et al., "Recent Trends of Bioceramics Research, Technology and Standardization"; Ceramics Japan, vol. 41 ,2006); pp. 549-553.
Maeda, et al., "Preparation of poly (L-lactic acid)-polysiloxane-calcium carbonate hybrid membrandes for guided bone regeneration"; Biomaterials, vol. 27 (2006); pp. 1216-1222.
Maeda, et al., "Preparation of Calcium Carbonate Composites and Their Apatite-Forming Ability in Simulated Body Fluid"; Journal of the Ceramic Society of Japan, vol. 122, Issue 5 (2004); pp. S804-S808.
Wakita, et al., "New Fabrication Process of Layered Membranes Based on Poly(Lactic Acid) Fibers for Guided Bone Regeneration"; Materials Transactions, vol. 50, Issue 7 (2009); pp. 1737-1741.
C. Murase, et al., "Preparation of three-dimensional poly (lactic acid) fiber scaffolds with silicon-releasability"; Nagoya Institute of Technology (with partial English translation) 2007; (2 pages).
Wakita, et al., "Preparation of layered membranes based on poly(lactic acid) fibers"; ISAEM-2008, Nagoya, Nov. 18-21, 2008; pp. 113-114.
Obata, et al., "PLA/Vaterite Composite Microfiber Membranes for GBR"; IUMRS-ICA 2008, Dec. 9-13, 2008, with partial English translation (2 pages).
Hotta, et al., "Preparation of poly(lactic acid) microfiber mats containing calcium carbonate particles by an electrospinning method"; 11th Symposium on Ceramics in Medicine, Biology and Biomimetrices, Dec. 7, 2007; with partial English translation; p. 15 (2 pages).
Ota, et al., "Development of Calcium Carbonate (Vaterite) and its Composites Useful for Biomimetics Apatite Coating"; Phosphorus Letter, No. 61, Feb. 1, 2008; pp. 33-37.
Obata, et al., "Poly(lactic acid) composites prepared using vaterite particles containing silicon species"; The Ceramic Society of Japan, 2008 Annual Conference, with partial English translation; p. 324.
Obata, et al., "Preparation of Microfibrous Mats Consisting of Calcium Carbonate/Poly(lactic acid) Composites"; The Japan Institute of Metals, 2008 Spring Conference, with partial English translation; p. 71 (2 pages).
Obata, et al., "Preparation of Fibrous Mats Consisting of Calcium Carbonate/Poly(Lactic Acid) Composites for Guided Bone Regeneration"; The Japan Institute of Metals, Spring Conference Mar. 2009, with partial English translation (2 pages).
Office Action issued Jul. 21, 2011 in related U.S. Appl. No. 12/591,258 (7 pages).
Office Action issued Sep. 16, 2011 in related U.S. Appl. No. 12/591,258 (14 pages).
Related U.S. Appl. No. 12/591,258, filed Nov. 13, 2009, in the name of Kasuga, et al. (46 pages).
Related U.S. Appl. No. 12/876,665, filed Sep. 7, 2010, in the name of Kasuga, et al. (33 pages).
Obata, et al., "Biocompatibilities of fibrous mats consisting of calcium carbonate/poly(lactic acid) hybrid materials with silicon-releasability"; The Symposium on Ceramics in Medicine, Biology and Biomimetics, Yokohama, Japan, Dec. 5, 2008, with partial English translation; p. 25 (2 pages).
Obata, et al., "Preparation of poly(lactic acid) calcium carbonate hybrid nonwoven for GBR"; General Sessions of The Japanese Society of Dental Materials and Devices, Apr. 11, 2009, with partial English translation; p. 43 (2 pages).
Murase, et al., "Preparation of three-dimensional poly (lactic acid) fiber scaffolds with silicon-releasability"; Nagoya Institute of Technology, Mar. 16, 2009 (with partial English translation) (2 pages).
Office Action issued May 10, 2012, in related U.S. Appl. No. 12/876,665 (13 pages).
Obata, A., et al., "Preparation of poly(lactic acid)Isilicon-doped calcium carbonate composite fibrous mats by electrospinning"; ISAEM-2008, Nagoya (Nov. 2008); p. 114.
"Fabric", n., Oxford English Dictionary/The definitive record of the English language, available at http://www.oed.com/view/Entry/6; (Jan. 11, 2012) (6 pages).
Office Action issued Jan. 19, 2012, in related U.S. Appl. No. 12/591,258 (18 pages.
Notice of Allowance dated Sep. 15, 2016, issued by the U.S. Patent and Trademark Office in related U.S. Appl. No. 14/728,544 (16 pages).

* cited by examiner

FIBER WADDING FOR FILLING BONE DEFECTS

CROSS REFERENCE TO RELATED APPLICATIONS

This application is continuation of U.S. patent application No. 13/350,569, filed on Jan. 13, 2012, now U.S. Pat. No. 8,853,298, which is a continuation-in-part application of U.S. patent application Ser. No. 12/707,302, filed on Feb. 17, 2010, now abandoned which claims the priority of Japanese Patent Application No. 2009-163320, filed on Jul. 10, 2009. The '569 application also claims the priority of Japanese Patent Application No. 2011-021790, filed on Feb. 3, 2011. The present application claims the benefits and priority of all these prior applications. The contents of these prior applications are incorporated herein by reference in their entireties.

FIELD OF THE INVENTION

The present invention relates to bioactive materials which are useful as bone-repairing materials for filling bone defects and may be used in the fields, such as oral or maxillofacial surgery and orthopedic surgery. More specifically, the present invention relates to a fiber wadding for filling bone defects. The fiber wadding has a three-dimensional structure and comprises a bioresorbable-biodegradable resin.

RELATED ART OF THE INVENTION

Some materials, when buried or implanted in bone defects, react with the bone and are directly chemically combined with the bone. These materials are called bioactive materials and are further classified into superficial bioactive materials, where the reaction occurs only on the surface of the materials; and bioresorbable materials, where the reaction occurs even inside the materials and the materials are gradually replaced with the bone. Exemplary commercialized superficial bioactive materials include hydroxyapatite ceramics (e.g., trade name APACERAM™ supplied by HOYA CORPORATION, Japan); and exemplary commercialized bioresorbable materials include beta phase tricalcium phosphate ceramics (e.g., trade name OSferion™ supplied by Olympus Terumo Biomaterials Corp., Japan).

Calcium carbonate ($CaCO_3$) and gypsum ($CaSO_4H_2O$) are also known to be bioresorbable. These substances, however, have low strength and toughness and are difficult to be machined. In contrast, biodegradable polymers such as poly(lactic acid)s, poly(glycolic acid)s, copolymers of them, and polycaprolactones are highly flexible and are easy to be machined. The biodegradable polymers, however, do not show osteogenic ability (bone forming ability) because their biodegradability is derived from the phenomenon that they are degraded in vivo and are discharged therefrom. In addition, there have been some reports that some of the biodegradable polymers may affect surrounding tissues because they are degraded typically into lactic acid or glycolic acid upon degradation and thus show acidity. Under such circumstances, there have been made investigations to provide composite materials between these inorganic compounds and organic compounds to allow the composite materials to have both osteogenic ability and bioresorbability and further have improved mechanical properties. For example, Japanese Unexamined Patent Application Publication (JP-A) No. 2001-294673 discloses a process for the preparation of a bioresorbable material by combining a poly (lactic acid) and a calcium carbonate. Specifically, this document refers to a process for synthesizing a bioresorbable material by mixing a calcium carbonate containing vaterite as a principal component with a biodegradable polymer compound such as a poly (lactic acid), which vaterite is highly soluble in water among such calcium carbonates. This technique is also advantageous in that the pH is always maintained around neutrality, because even when the poly (lactic acid) is decomposed to be acidic, the acidity is neutralized by the buffering effects of the calcium carbonate as dissolved.

In this unprecedented aged society, bone defects should be desirably cured as soon as possible, because it is very important to maintain and ensure mastication and exercise performance for the health maintenance. To improve osteogenic ability, there have been attempted to incorporate, to a bioresorbable membrane, a factor such as a bone formation inducer (see Japanese Unexamined Patent Application Publication (JP-A) No. H06 (1994)-319794), or a proliferation factor or a bone morphogenic protein (see Japanese Unexamined Patent Application Publication (Translation of PCT Application) (JP-A) No. 2001-519210; and Japanese Unexamined Patent Application Publication (JP-A) No. 2006-187303). However, it is difficult to handle these factors. Accordingly, demands have been made to develop a bioresorbable material having superior bone reconstruction ability to allow the bone to self-regenerate more reliably and more rapidly.

In view of recent trends of researches and technologies for bio-related materials, the main stream of researches has been shifted from a materials design for the bonding of a material with the bone to a materials design for the regeneration of the bone; in these researches, the role of silicon in bone formation has received much attention; and a variety of silicon-doped materials have been designed (TSURU Kanji, OGAWA Tetsuro, and OGUSHI Hajime, "Recent Trends of Bioceramics Research, Technology and Standardization", Ceramics Japan, 41, 549-553 (2006)). For example, there has been reported that the controlled release of silicon can act on cells to promote bone formation (H. Maeda, T. Kasuga, and L. L. Hench, "Preparation of Poly(L-lactic acid)-Polysiloxane-Calcium Carbonate Hybrid Membranes for Guided Bone Regeneration", Biomaterials, 27, 1216-1222 (2006)). Independently, when composites of a poly (lactic acid) with one of three types of calcium carbonates (calcite, aragonite, and vaterite) are prepared and soaked in a simulated body fluid (SBF), the composite of the poly (lactic acid) with vaterite forms a hydroxyapatite having bone-like composition and dimensions within a shortest time among the three composites (H. Maeda, T. Kasuga, M. Nogami, and Y Ota, "Preparation of Calcium Carbonate Composite and Their Apatite-Forming Ability in Simulated Body Fluid", J. Ceram. Soc. Japan, 112, S804-808 (2004)). These findings demonstrate that the use of vaterite, which can gradually release silicon, is believed to be a key to provide a material that produces more rapid bone reconstruction.

To use a material for filling bone defects, the affected area (bone defect) is incised and a dense or porous material, having such a size as to fill the affected area sufficiently, is directly implanted therein, or a granular material is charged into the affected area.

To ensure bone formation, it is desirable to implant or bury such a material in the affected area without a gap (clearance). However, it is not easy to process a dense or porous material so as to fit the dimensions of the affected area snuggly. In addition, a granular material, if charged into the affected area, often drops off from the affected area after the surgery (implantation). These techniques are therefore susceptible to improvements.

Independently, there is also known a guided bone regeneration technique that uses a masking membrane to cover a bone defect. The guided bone regeneration technique does not involve charging a material into the affected area. Instead, this techniques uses a masking membrane, which has the functions of preventing the invasion of cells and tissues not involved in bone formation into the bone defect, allowing the self-regeneration ability of the bone to exhibit, and helping the bone to reconstruct. This technique is intended to cure the bone defect by using the curing ability that a living body inherently has. For example, Japanese Unexamined Patent Application Publication (JP-A) No. 2009-61109 discloses a guided bone regeneration membrane and a production method thereof, wherein guided bone regeneration membrane has a bi-layer structure including a first nonwoven fabric layer and a second nonwoven fabric layer, in which the first nonwoven fabric layer contains a silicon-releasable calcium carbonate and a biodegradable resin as principal components, and the second nonwoven fabric layer contains a biodegradable resin as a principal component. It has been reported that the use of this membrane gives satisfactory proliferation of murine osteoblast-like cells (MC3T3-E1 cells), and when a bone defect formed in a rabbit cranial bone is covered by such a membrane, satisfactory bone formation (osteogenesis) is observed (see T. Wakita, A. Obata and T. Kasuga, "New Fabrication Process of Layered Membranes Based on Poly (Lactic Acid) Fibers for Guided Bone Regeneration", Materials Transactions, 50 [7], 1737-1741 (2009)). This membrane, however, is not usable as a material for filling bone defects because it has a small thickness of from 230 to 300 µm. In addition, the bulk density of such membranes, estimated to be about 0.4 g/cm$^3$ or more, is generally too high to be used as a material for filling bone defects.

SUMMARY OF THE INVENTION

Accordingly, an object of the present invention is to provide a fiber wadding formed of a bioresorbable material for filling bone defects, which material may have a sustained release system with such a chemical composition as to guide bone reconstruction ability effectively and has a three-dimensional structure having such a flexibility as to fit in an affected area satisfactorily.

In one aspect, the present invention relates to a fiber wadding for filling bone defects, wherein the fiber wadding having a flocculent three-dimensional structure including a plurality of fibers. The fibers contain a biodegradable resin as a principal component and contain or bear a siloxane.

In one aspect, fibers in a fiber wadding of the invention may be coated with hydroxyapatite on their surfaces. The biodegradable resin may be poly(lactic acid) or a copolymer thereof. The fibers may contain siloxane dispersed in calcium carbonate micro-particles.

In one aspect, the present invention relates a fiber wadding for filling bone defects comprising a plurality of fibers comprising a biodegradable resin and vaterite phase calcium carbonate micro-particles, wherein the plurality of fibers are entangled with each other in three dimensional directions to form a fiber wadding such that a bulk density of the fiber wadding is 0.005-0.3 g/cm$^3$.

BRIEF DESCRIPTION OF THE DRAWINGS

Other objects, features and advantages of the present invention will be understood more fully from the following detailed description made with reference to the accompanying drawings.

In the drawings:

FIG. 13 (B) shows an explanatory view of measurement of compressibility of the fiber wadding prepared in Example 3, in which a weight is placed on a cover. FIG. 13 (C) is an explanatory view of measurement of compression recovery of the fiber wadding prepared in Example 3, in which the weight is removed from the cover.

DETAILED DESCRIPTION

Figure 1:
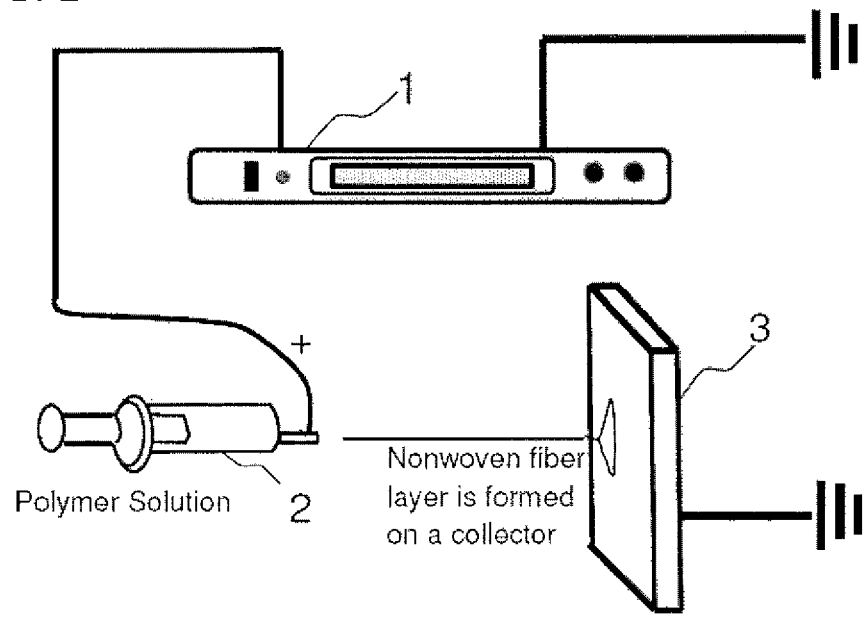
FIG. 1 shows an explanatory view of a common electrospinning technique.

The present invention will be described further with reference to various embodiments in the drawings. Embodiments of the present invention relates to bioactive materials for filling bone defects. The materials comprise fiber wadding. Such a material has a flocculent three-dimensional structure of a fibrous substance that comprises a biodegradable resin as a principal component. The fibrous substance contains or bears a siloxane.

As used herein, a flocculent three-dimensional (3D) structure is a loose fluffy 3D structure. A biomaterial of the invention having such a loose fluffy 3D structure may be defined by various physical/chemical parameters, such as its weight, bulk density, compressibility, compression recovery ability, as described herein. These physical/chemical parameters may be determined using known standard methods, such as the Japanese Industrial Standard (JIS) methods, particularly JIS L 1097 method.

A siloxane is any chemical compound composed of units of the form $(R_2SiO)_n$, where R is a hydrogen atom or a hydrocarbon group. Siloxane has a backbone comprising alternating Si and O. A siloxane suitable for use with embodiments of the invention can be any siloxane that can release Si in vivo.

Bioactive materials of the invention may be prepared using electrospinning techniques. Electrospinning uses an electrical charge to draw very fine (typically on the micro or nano scale) fibers from a liquid or a slurry. When a sufficiently high voltage is applied to a liquid droplet, the body of the liquid becomes charged. The electrostatic repulsion in the droplet would counteract the surface tension and the droplet is stretched. When the repulsion force exceeds the surface tension, a stream of liquid erupts from the surface. This point of eruption is known as a Taylor cone. If molecular cohesion of the liquid is sufficiently high, the stream does not breakup and a charged liquid jet is formed. As the jet dries in flight, the mode of current flow changes from ohmic to convective as the charge migrates to the surface of the fiber. The jet is then elongated by a whipping process caused by electrostatic repulsion initiated at small bends in the fiber, until it is finally deposited on a grounded collector. The elongation and thinning of the fiber resulting from this bending instability leads to the formation of uniform fibers with nanometer-scale diameters.

While the voltage is normally applied to the solution or slurry in a regular electrospinning process, according to embodiments of the present invention, the voltage is applied to the collector, not to the polymer solution (or slurry), and, therefore, the polymer solution is grounded. The polymer solution or slurry is sprayed into fibers while applying the voltage in this manner, and the fibers are entangled to form a three-dimensional structure.

Alternatively, a material for filling bone defects having a three-dimensional structure and being satisfactorily flexible can also be obtained by carrying out the improved electrospinning technique, followed by soaking the electrospun material in a buffer solution that is supersaturated with hydroxyapatite.

Examples of biodegradable resins usable with embodiments of the invention include synthetic polymers, such as polyethylene glycols (PEGs), polycaprolactones (PCLs), poly(lactic acids) (PLAs), polyglycolic acids (PGAs), and copolymers of PEG and PCL; and natural polymers, such as fibrin, collagen, alginic acid, hyaluronic acid, chitin, and chitosan. Preferred examples of the biodegradable resin include a poly(lactic acid) (PLA); and a copolymer of a poly(lactic acid) and a poly(glycolic acid) (PGA) (i.e., lactic acid-glycolic acid copolymer).

According to embodiments of the invention, a material for filling bone defects may be produced in the following manner. Initially, a solution is prepared by dissolving a biodegradable resin (such as PLA) in a suitable solvent, e.g., chloroform ($CHCl_3$) and/or dichloromethane. An aqueous solution of aminopropyltriethoxysilane (APTES) is added to the solution. In this procedure, the weight ratio of PLA:APTES (PLA to APTES) is possibly from 1:0.01 to 1:0.5, but is preferably from 1:0.01 to 1:0.05 (by weight). This is because most of APTES, if added in an excessively large amount, is dissolved out in early stages of soaking in the aqueous solution and, therefore, not so effective. The PLA has a molecular weight of from about $20 \times 10^4$ to about $30 \times 10^4$ kDa. The concentration of the PLA in the solution is preferably from 4 to 12 percent by weight for satisfactory spinning. To maintain satisfactory spinning conditions, dimethylformamide and/or methanol may be added to the solution in a proportion of about 50 percent by weight or less relative to chloroform and/or dichloromethane.

A liquid having a greater relative dielectric constant than that of the biodegradable resin may be added to the resulting solution to produce a spinning solution for the preparation of a three-dimensional structure. Typically, when the biodegradable resin is a poly (lactic acid), a liquid having a greater relative dielectric constant than that of lactic acid may be added. Examples of the liquids having a greater relative dielectric constant than that of lactic acid (relative dielectric constant: 22.0) include methanol (relative dielectric constant: 32.6), ethanol (relative dielectric constant: 24.6), ethylene glycol (relative dielectric constant: 37.7), 1,2-propanediol (relative dielectric constant: 32.0), 2,3-butanediol, glycerol (relative dielectric constant: 42.5), acetonitrile (relative dielectric constant: 37.5), propionitrile (relative dielectric constant: 29.7), benzonitrile (relative dielectric constant: 25.2), sulfolane (relative dielectric constant: 43.3), and nitromethane (relative dielectric constant: 35.9). Any of these are effective, but most advantageously water (relative dielectric constant: 70 to 80) may be used. However, water is immiscible with and completely separated from chloroform and/or dichloromethane used as a solvent for the PLA. To avoid this problem, an amphiphilic liquid, such as methanol, ethanol, propanol, and/or acetone, is preferably in coexistence with the solvent and water. Such amphiphilic liquids for use herein are not limited in their relative dielectric constants, as long as they are amphiphilic and satisfactorily miscible both with the solvent (such as chloroform and/or dichloromethane) and water. As an example, 0.5 to 5 g of the amphiphilic liquid (such as methanol, ethanol, propanol, and/or acetone) and 0.5 to 3 g of water may be added per 1 g of the PLA.

A spinning solution may be further combined with a calcium carbonate to form a slurry (spinning slurry). This helps to speedup (acceleration) the step of soaking the electrospun article in a buffer solution that is supersaturated with hydroxyapatite to form an absorbable hydroxyapatite thereon. The absorbable hydroxyapatite helps to confer higher initial cellular adhesion. The amount of the calcium carbonate is possibly 60 percent by weight or less, because the calcium carbonate, if added in an amount of more than 60 percent by weight, maybe difficult to mix with the solution to give a homogeneous slurry. However, the calcium carbonate, if added in an amount less than 10 percent by weight, may not exhibit its advantageous effects remarkably. The solution or slurry may further include one or more inorganic substances which are usable in vivo without problems. Examples of such inorganic substances include hydroxyapatite, tricalcium phosphate, calcium sulfate, sodium phosphate, sodium hydrogen phosphate, calcium hydrogen phosphate, octacalcium phosphate, tetracalcium phosphate, calcium pyrophosphate, and calcium chloride.

In accordance with embodiments of the invention, a material for filling bone defects can also be a substance containing a biodegradable resin as a principal component and further containing or bearing a siloxane. This substance may be prepared by preparing calcium carbonate microparticles bearing siloxane dispersed therein ($Si—CaCO_3$), typically by the method described in Japanese Unexamined Patent Application Publication (JP-A) No. 2008-100878; and mixing 60 percent by weight or less of the $Si—CaCO_3$ microparticles with PLA. The amount of the Si—CaCO$_3$ microparticles is preferably from 10 to 60 percent by weight relative to the PLA, as in the calcium carbonate. To uniformly disperse the micro-particles, the substance is preferably prepared by kneading the PLA and Si—CaCO$_3$ microparticles in predetermined proportions in a heating kneader to give a composite. The composite is then dissolved in the solvent to give a spinning solution.

According to a common electrospinning technique, as illustrated in FIG. 1, a charge is applied by a voltage supply 1 to a nozzle of a syringe 2. In this manner, a positive charge is applied to a spinning solution; and the solution is slowly extruded from the tip of the nozzle. When the effect of electric field becomes larger than the surface tension, the solution is stretched into fibers and travels toward a collector 3 which is connected with a ground electrode. On the way to the collector 3, the solvent of the solution evaporates, thereby forming a thin layer of nonwoven fabric of fibers. This technique, however, does not produce a three-dimensional structure, even if one modifies the spinning conditions (such as the concentration of the spinning solution, the type of solvent contained in the solution, the supply speed of the solution, the spinning time, the applied voltage, and the distance between the nozzle and the collector). This is because the residual solution and the resin deposited on the collector 3 are charged by themselves and repel each other. The repulsion impedes the deposition in a thickness direction. In this connection, the fibrous resin derived from the solution deposits on the collector 3 would have most solvent evaporated. However, a trace amount of the solution deposits intact (i.e., containing the solvent) on the collector 3.

Figure 2:
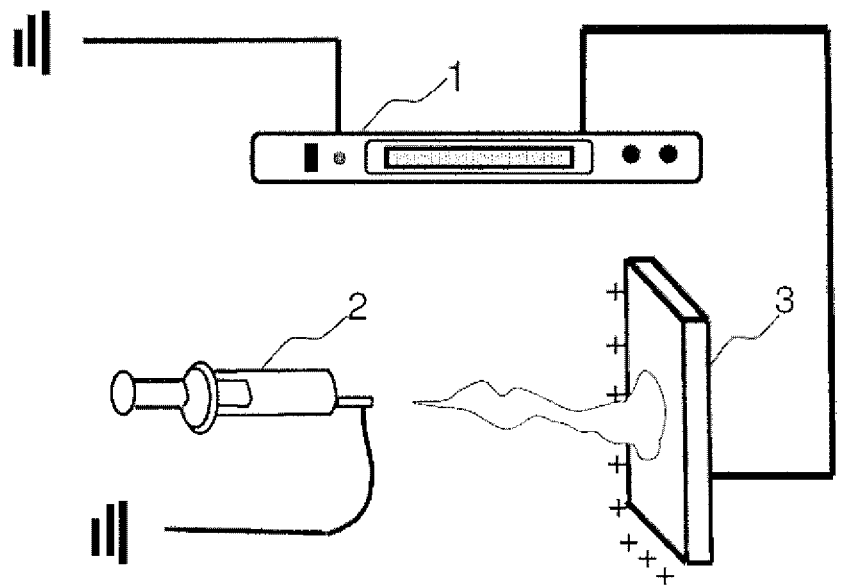
FIG. 2 shows an explanatory view of an electrospinning technique according to an embodiment of the present invention.

In contrast, according to embodiments of the present invention, as illustrated in FIG. 2, a three-dimensional structure of a fiber wadding can be formed by carrying out electrospinning while grounding the nozzle of the syringe 2 (i.e., without applying a charge thereto). At the same time, a positive charge is applied to the collector 3. According this technique, if a regular spinning solution is slowly extruded from the tip of the nozzle, the spinning solution would fall as droplets, because the solution is not charged. However, when the spinning solution further contains a liquid, such as water, having a greater relative dielectric constant than that of the biodegradable resin, the liquid may be affected by the electric field, and the spinning solution may be drawn toward the collector by the action of polarization. In this case, the spinning solution is not charged by itself and readily forms three-dimensional deposits on the collector 3, without suffering from electrostatic repulsion. In this process, the liquid (solution) may be divided into two or more strands and drawn from the nozzle of the syringe 2 toward the collector 3. These strands are entangled to form a flocculent three-dimensional structure on the collector 3.

To allow this phenomenon to occur, however, the spinning solution should have a somewhat low viscosity. If the spinning solution has an excessively high viscosity, it may not reach the collector 3 even when affected by the electric field. Accordingly, the diameter of the fibrous substance constituting the three-dimensional structure prepared according to embodiments of the invention may be substantially controlled by the viscosity of the spinning solution. When the spinning solution has a particularly low viscosity, the fibrous substance can deposit more easily to form a three-dimensional structure and the fibrous substance would more likely have smaller fiber diameters. Typically, when a spinning solution is prepared by dissolving PLA in chloroform to give a solution, followed by adding ethanol and water thereto, the resulting fibrous substance has a fiber diameter in a range of about 0.05 μm to about 10 μm. It is acceptable not to apply a positive charge, but a negative charge, to the collector 3, as long as the spinning solution can be drawn toward the collector by the action of polarization.

The resulting three-dimensional structure of a fiber wadding may be cut into a piece of a required size, and the cut piece may be soaked in a buffer solution, containing calcium ions and phosphate ions and being saturated with respect to hydroxyapatite, to coat the surface of the fibrous skeleton with hydroxyapatite. Examples of the buffer solution for use herein include a Tris buffer solution (pH 7.2 to 7.4) containing ions at a concentration substantially equal to the inorganic ion concentration in human plasma (simulated body fluid, or SBF) and a solution (1.5 SBF) containing ions in concentrations 1.5 times those of SBF. The 1.5 SBF is more advantageous, because the fibrous substance can be coated with hydroxyapatite more rapidly.

According to the present embodiment, there is provided a flexible material for filling bone defects, which material has a three-dimensional structure of a fiber wadding including a fibrous substance, in which the fibrous substance contains a biodegradable resin, represented by poly(lactic acid) (PLA), as a principal component, and further contains or bears siloxane. There is also provided a filling material for bone-repairing, in which the surface of the fibrous substance constituting the three-dimensional structure is coated with hydroxyapatite. Such a material, which includes communicating space for the entrance of cells and has improved fitability in the affected area, can be easily prepared by adopting the technique for producing a nonwoven fabric through electro spinning to the production of the three-dimensional structure. In addition, the coating with an absorbable hydroxyapatite can be easily performed by soaking the electrospun article in a buffer solution supersaturated with hydroxyapatite, and the coated absorbable hydroxyapatite helps to provide higher initial cellular adhesion.

A fiber wadding for filling bone defects thus obtained has satisfactory flexibility derived from the three-dimensional structure constituted by the fibrous substance. Such fiber wadding shows high cell proliferation in cellular affinity assay using osteoblast-like cells (MC3T3-E1 cells) and excels in bone reconstruction ability. Bulk density of the fiber wadding of this embodiment is much lower than masking membrane of prior art as disclosed, for example, by JP-A 2009-61109.

According to the some embodiments of the present invention, fibers of the fiber wadding are formed of a composite of silicon-releasable calcium carbonate and a biodegradable polymer.

Figure 11:
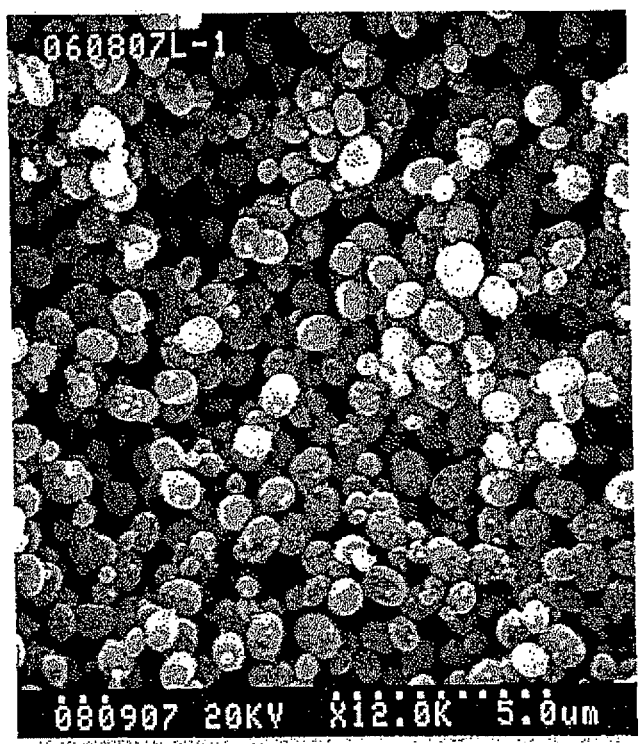
FIG. 11 shows a SEM photo of micro-particles of a silicon releasable calcium carbonate obtained by carbonation process.

Similarly to the exemplary embodiment discussed above, micro-particles of calcium carbonate of vaterite phase may be used as Si-releasable calcium carbonate, Si content of which may be, for example, 2 wt % (herein after referred to as 2SiV). As disclosed in detail in the Japanese Unexamined Patent Application Publication (JP-A) No. 2008-100878, Si releasable calcium carbonate can be obtained by using carbonation process, in which carbonate gas is sprayed into a suspension of a mixture of methanol, slaked lime, and organic silicon compound. FIG. 11 shows an SEM photo of the micro-particles of calcium carbonate, which is disclosed in the (JP-A) No. 2008-100878. Although diameters of the micro-particles vary and may be changed by adjusting the production conditions, preferable range of the diameter of the micro-particles are approximately 0.5-1.5 μm.

A composite of silicone releasable calcium carbonate and biodegradable polymer may be formed by heating/kneading a mixture of Silicon vaterite powders and polylactic acid or a copolymer of polylactic acid and polyglycolic acid. Molecular weights of the polylactic acid or a copolymer of polylactic acid and polyglycolic acid are preferably from 150000 to 300000. In order to obtain a desirable elasticity of the fiber wadding, the 2SiV content of the composite is preferably 30-40 wt %. This composite may be dissolved using a solvent (such as $CHCL_3$) to obtain a spinning solution. The spinning solution thus obtained may be processed into a fiber wadding using electrospinning techniques.

Figure 12:
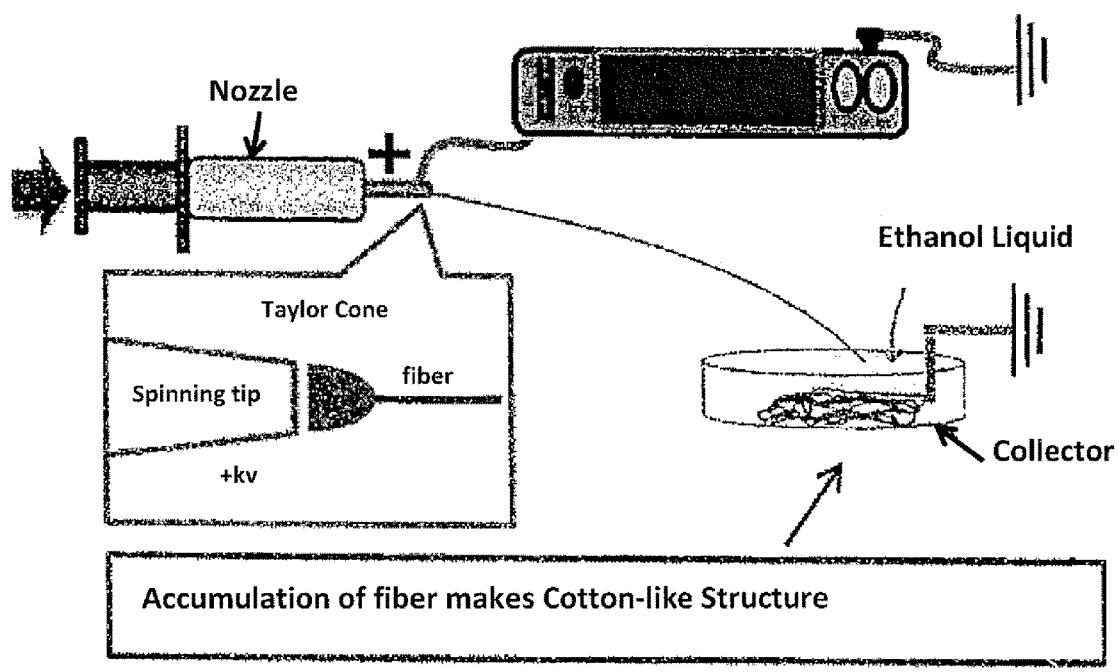
FIG. 12 shows an explanatory view of an electrospinning technique according to an embodiment of the present invention.

To process the spinning solution into fiber wadding using electrospinning, as illustrated in FIG. 12, a positive voltage is applied to the spinning solution in a state that a container of the collector filled with ethanol is grounded. The spinning solution is then made into fibers and the electrospun fibers are attracted and travel to the container of the collector, while solvent of the spinning solution is evaporated in the electric field during that process. Those fibers attracted to the container of the collector are accumulated in the ethanol of the container to form a cotton like structure. By changing the spinning conditions (such as the density of the spinning solution, kinds of solvent, supply speed, time period of electrospinning, the voltage applied, the distance between the nozzle and ethanol in the container of the collector), desired morphology of the fiber wadding can be achieved.

Outside diameter of fiber wadding of this embodiment is preferably from about 0.05 μm to about 30 μm, preferably from about 0.1 μm to about 20 μm, and more preferably from about 10 μm to about 20 μm. Bulk density of fiber wadding as measured in accordance with JIS L 1097 is from about 0.005 $g/cm^3$ to about 0.3 $g/cm^3$, preferably from about 0.01 $g/cm^3$ to about 0.1 $g/cm^3$, more preferably from about 0.014 $g/cm^3$ to about 0.021 $g/cm^3$. Compressibility of the fiber wadding of this embodiment is from about 10% to about 55%, preferably from about 20% to about 55%, more preferably from 29% to 55%. Compression recovery of the fiber wadding of this embodiment is from about 5% to about 76%, preferably from about 7% to about 76%, more preferably from about 44% to about 58%.

ADVANTAGE OF THE INVENTION

Because fiber wadding of the present invention is formed of Si releasable calcium carbonate and a biodegradable polymer, it shows high cell proliferation, and has an excellent bone reconstruction ability. Compared with masking membrane, the bulk density of a fiber wadding of the present invention is very low. In addition, a fiber wadding of the invention is flexible and has excellent elasticity. Therefore, it can be easily filled in the bone defects during surgery and can be implanted in the bone defects without gap (clearance).

EXAMPLE 1 and EXAMPLE 2

The present invention will be illustrated in further in detail with reference to several examples below, which relate to production methods of three-dimensional structures. It should be noted, however, that these examples are illustrated for better understanding of the present invention and are never intended to limit the scope of the present invention. One skilled in the art would appreciate that various modifications are possible without departing from the scope of the invention.

Raw Materials Used in Example 1 and Example 2

Poly(lactic acid) (PLA): PURASORB PL Poly(L-lactide), having a molecular weight of from $20 \times 10^4$ to $30 \times 10^4$, is from PURAC Biochem (a division of CSM; Netherlands). Chloroform ($CHCl_3$): analytical grade reagent, with a purity of 99.0% or more, is from Kishida Chemical Co., Ltd., Japan. γ-Aminopropyltriethoxysilane (APTES): (TSL8331, with a purity of 98% or more, GE Toshiba Silicones Co., Ltd., Japan).

Siloxane-doped calcium carbonate (Si—$CaCO_3$): Vaterite containing a siloxane in terms of a silicon ion content of 2.9 percent by weight and prepared by using slaked lime (Microstar T; with a purity of 96% or more; Yabashi Industries Co., Ltd., Japan), methanol (analytical grade reagent; with a purity of 99.8% or more; Kishida Chemical Co., Ltd., Japan), APTES, and carbon dioxide gas (high-purity liquefied carbon dioxide gas; with a purity of 99.9%; Taiyo Kagaku Kogyo K.K., Japan).

Electrospinning Conditions in Example 1 and Example 2

Spinning solution feed rate: 0.1 ml/min,

Applied voltage: A voltage was applied to the plate collector at 25 kV, while the nozzle being grounded, Distance between the nozzle and the plate collector: 100 mm, Spinning time: about 60 minutes

EXAMPLE 1

APTES (1 g) was added to ultrapure water (0.5 g) with stirring to give a solution. The solution was added dropwise to an 8% by weight PLA solution in $CHCl_3$ so as to give an APTES content of 0.015 g and 0.050 g, respectively, followed by stirring. During this procedure, APTES was condensed to give a siloxane. To the resulting mixtures were added 1.5 g of ethanol and 1 g of ultrapure water to give spinning solutions. These spinning solutions were subjected to electrospinning and thereby yielded three-dimensional structures each including a fibrous substance containing a biodegradable resin as a principal component and containing or bearing a siloxane (hereinafter these steric structures are referred to as Si-$PLA_{15}$ and Si-$PLA_{50}$, respectively).

Figure 3:
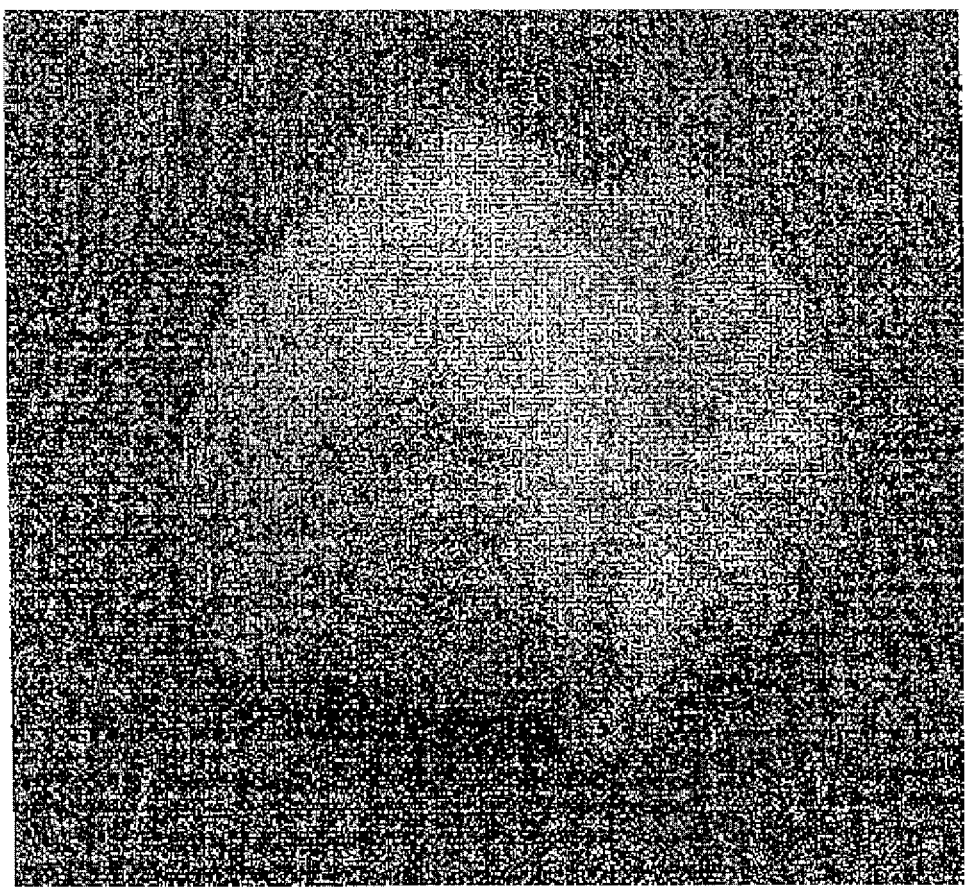
FIG. 3 depicts the appearance of a three-dimensional structure of a fiber wadding prepared in Example 1, indicated with 10-mm squares.
Figure 4:
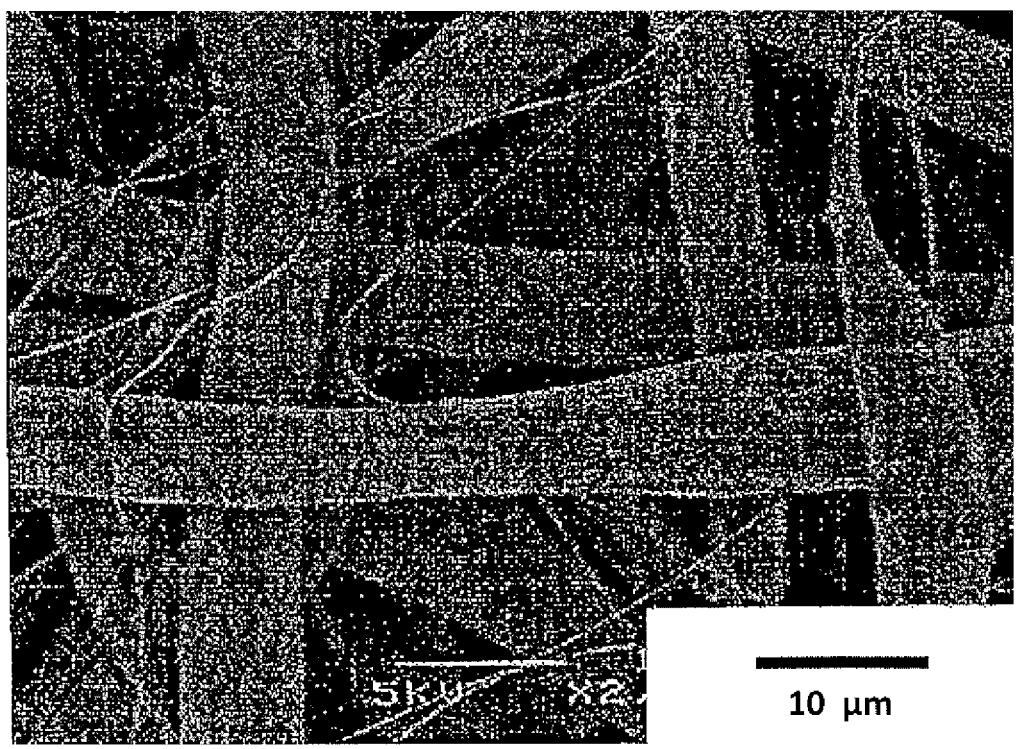
FIG. 4 shows a scanning electron micrograph (SEM) of fibers constituting the three-dimensional structure of a fiber wadding prepared in Example 1.

FIG. 3 depicts the appearance of the resulting three-dimensional structure (Si-$PLA_{15}$). FIG. 4 shows a scanning electron micrograph (SEM) of this steric structure, demonstrating that the steric structure is a flocculent structure including fibers having diameters of from several tens of nanometers to eight micrometers. The structures under this condition had a weight of 40 mg. The structures did not lose their flexibility and elasticity even after they were soaked in a cell culture medium and recovered therefrom.

Figure 5:
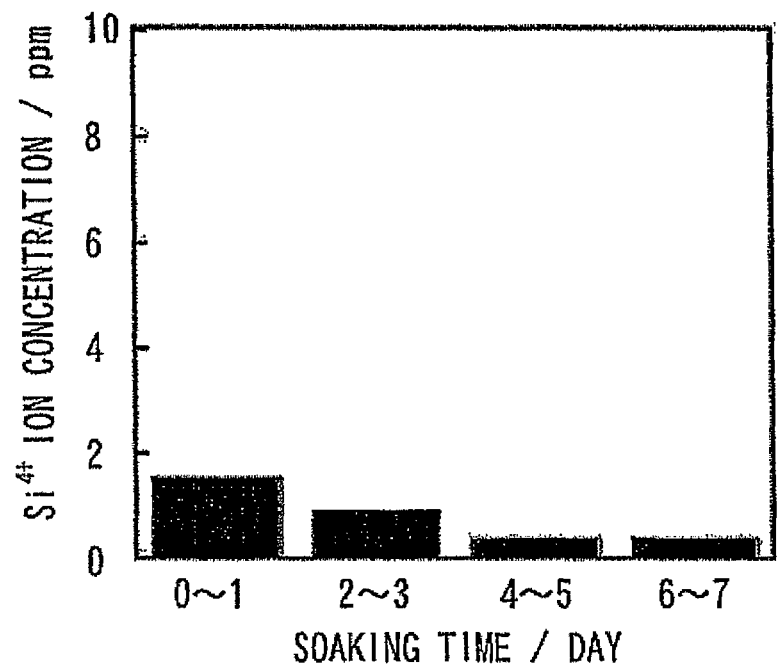
FIG. 5 is a graph showing the amounts of silicon ions released from a three-dimensional structure of Si-PLA$_{15}$, prepared in Example 1, into a cell culture medium.
Figure 6:
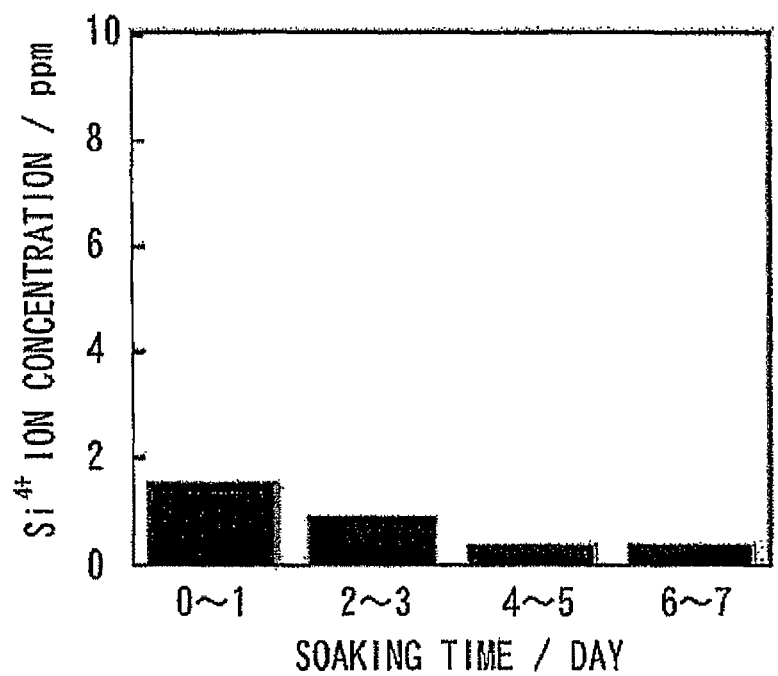
FIG. 6 is a graph showing the amounts of silicon ions released from a three-dimensional structure of Si-PLA$_{50}$, prepared in Example 1, into a cell culture medium.

Each of the above-prepared steric structures was cut to a piece 10 mm wide, 10 mm long, and 1 mm thick, soaked in 4 ml of cell culture medium α-MEM, held at a temperature of 37° C. in an incubator in an atmosphere of 5% carbon dioxide gas, and the cell culture medium was exchanged with fresh one on Day 1, Day 3, and Day 5. FIG. 5 and FIG. 6 show the release amounts of silicon ions when the steric structures were soaked in the cell culture medium as measured through inductively coupled plasma emission spectrometry. The data demonstrate that both the samples (steric structures) released a large amount of silicon ions on Day 1, and thereafter released silicon ions in a significantly decreased amount, but continued to release silicon ions at least up to Day 7. Si-$PLA_{50}$ released about 6.5 ppm of silicon ions on Day 1 but released 1 ppm or less of silicon ions from Day 6 to Day 7, showing only a slight difference from that in Si-$PLA_{15}$.

EXAMPLE 2

A Si—CaCO$_3$/PLA three-dimensional structure was prepared by kneading PLA and Si—CaCO$_3$ in a heating kneader at 200° C. for 15 minutes to give a Si—CaCO$_3$/PLA composite containing 40 percent by weight of Si—CaCO$_3$; mixing 1.67 g of the Si—CaCO$_3$/PLA composite with 8.33 g of CHCl$_3$ to give a solution; adding 1.5 g of ethanol and 1 g of ultrapure water to the solution to give a spinning solution; and subjecting the spinning solution to electrospinning under the above-mentioned conditions.

Figure 7:
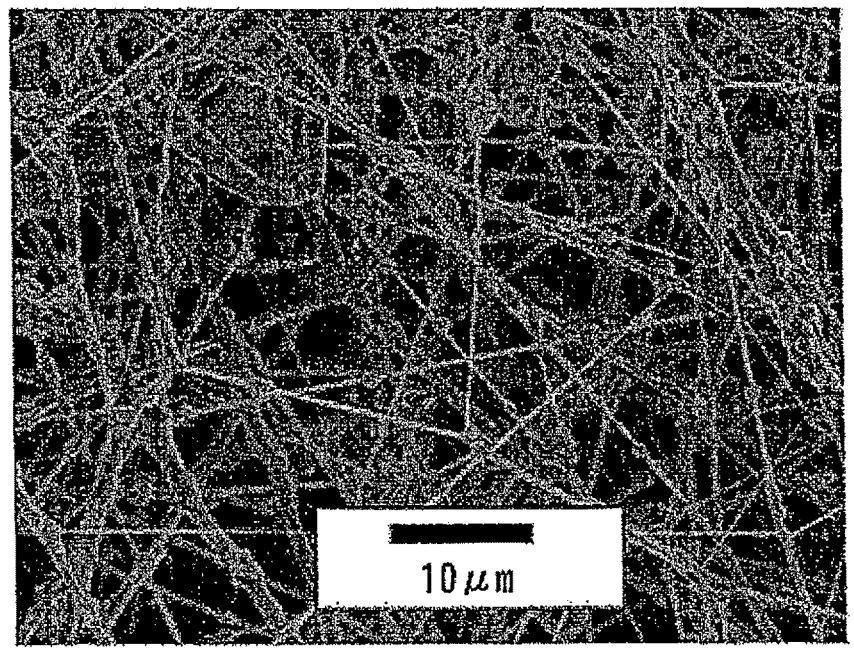
FIG. 7 shows a scanning electron micrograph (SEM) of fibers constituting a Si—CaCO$_3$/PLA three-dimensional structure prepared in Example 2.

The prepared three-dimensional structure has a flocculent appearance substantially the same as that shown in FIG. 3 and had superior flexibility and elasticity. FIG. 7 is a scanning electron micrograph (SEM) of the Si—CaCO$_3$/PLA three-dimensional structure, demonstrating that this steric structure is a structure including fine fibers having diameters of about 0.1 to about 3 μm and spherical calcium carbonate particles having diameters of about fpm embedded between the fibers. The fibers have small diameters, and spaces (clearances) between fibers are sufficiently large of about several tens of micrometers or more so as to give sufficient spaces to allow cells to enter therein. The release amount of silicon ions from this steric structure was determined by the procedure of Example 1 to find that the steric structure released silicon ions in amounts of 5.3 ppm on Day 1, 0.8 ppm from Day 2 to Day 3; 0.4 ppm from Day 4 to Day 5; and 0.4 ppm from Day 6 to Day 7, indicating that the release in trace amount of silicon ion continued.

Figure 8:
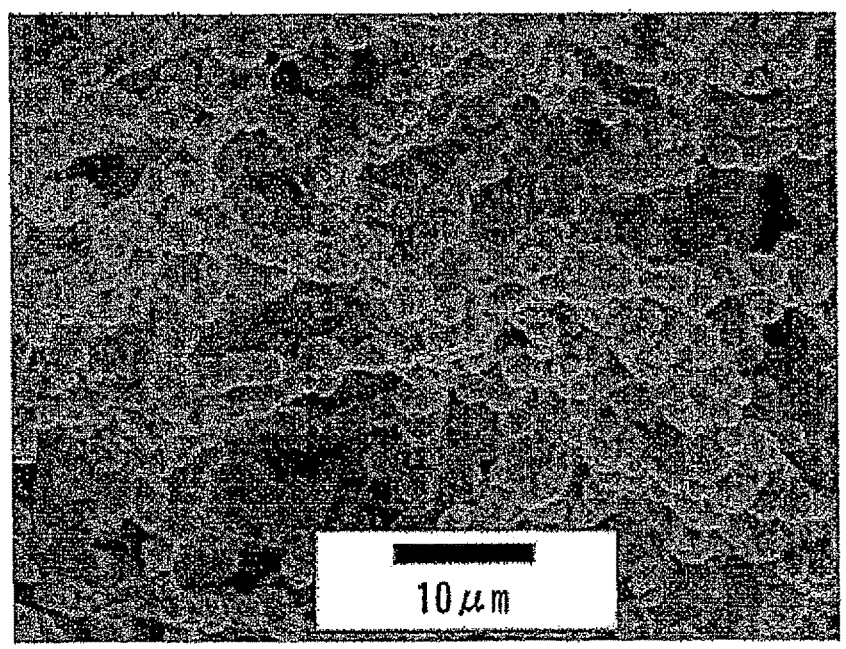
FIG. 8 shows a scanning electron micrograph (SEM) of fibers constituting a Si—CaCO$_3$/PLA three-dimensional structure obtained after soaking in 1.5 SBF, the Si—CaCO$_3$/PLA three-dimensional structure prepared in Example 2.
Figure 9:
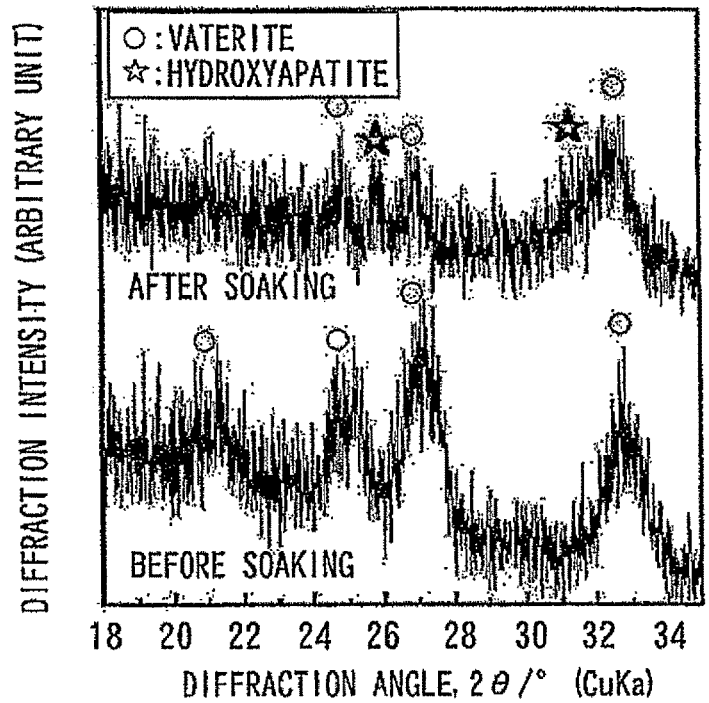
FIG. 9 depicts an X-ray diffraction patterns of the Si—CaCO$_3$/PLA three-dimensional structure prepared in Example 2, before and after soaking in 1.5 SBF.

The steric structure was cut to a sample piece 10 mm wide 10 mm long and 10 mm thick, soaked in 40 ml of 1.5 SBF, and held at 37° C. for one day. The sample piece was thereafter recovered from 1.5 SBF and observed under a scanning electron microscope (SEM), to find that a large number of aggregated particles as shown in FIG. 8 precipitated and that there remained spaces of about several tens of micrometers so as to allow cells to enter therein. FIG. 9 shows X-ray diffraction patterns of the sample piece before and after soaking in the 1.5 SBF, demonstrating that peaks derived from hydroxyapatite were observed in the sample piece after the soaking. These results demonstrate that the surfaces of fibers constituting the Si—CaCO$_3$/PLA three-dimensional steric structure can be easily coated with a hydroxyapatite merely by soaking the steric structure in 1.5 SBF.

Figure 10:
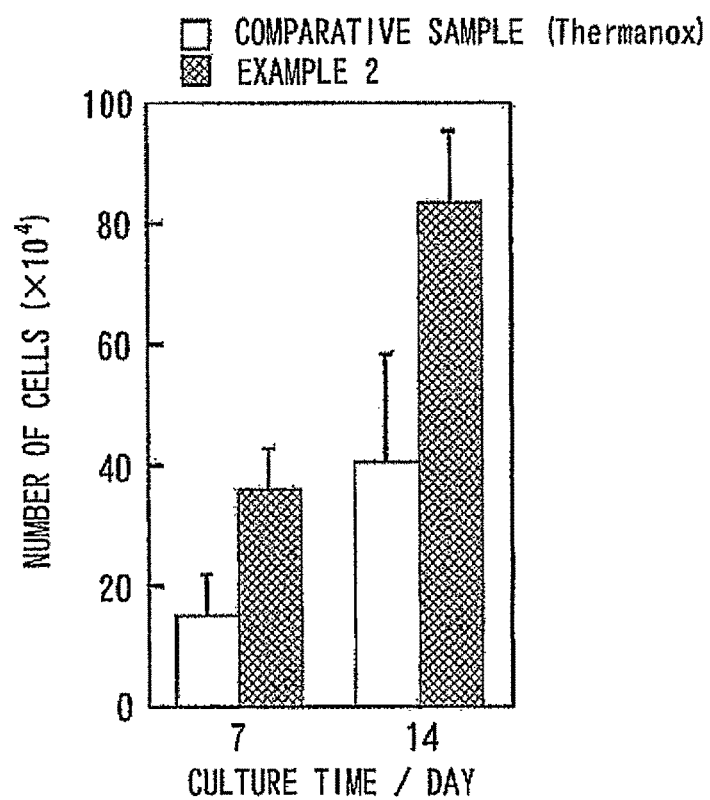
FIG. 10 is a graph showing the results in cell proliferation testing of a Si—CaCO$_3$/PLA three-dimensional structure coated with hydroxyapatite prepared in Example 2 and of a comparative sample.

FIG. 10 shows how cellular numbers (in terms of cellular numbers per 1 cm$^2$) vary after the inoculation of murine osteoblast-like cells (MC3T3-E1) on the hydroxyapatite-coated steric structure and on a comparative sample (Thermanox: plastic disc for cell culture). The comparative sample Thermanox had been treated on its surface for improving cell proliferation and for use in cell culture. The data in FIG. 10 demonstrate that the steric structure gives much higher cell growth capability than that of the surface-treated comparative sample and is expected as a material which excels in bone reconstruction ability.

Conditions for Cell Culture Experiment

Cultivation

Cultivation using 24-well plate,
Cell type: murine osteoblast-like cells (MC3T3-E1 cells; Riken Institute of Physical and Chemical Research, Japan).
Cell inoculation number: 1.times.10.sup.4 cells/well
Medium: α-MEM (containing 10% fetal bovine serum)
Medium exchange: on the day following the inoculation, thereafter every other day
Sample piece: The sample steric structure was cut to a piece 10 mm long, 10 mm wide, and 10 mm thick (10-mm cube)
Cell counting method: The measurement was performed using the Cell Counting Kit-8 (cellular growth/cellular toxicity analytical reagent; Dojindo Laboratories, Japan) in accordance with the protocol attached to the reagent.

EXAMPLE 3

Calcium carbonate of vaterite phase (18 g) having a Silicon content of 2 wt % (2SiV) and medical grade polylactic acid (42 g) were mixed and heated/kneaded at 200° C. for 45 minutes. This is then cooled to obtain a composite (SiPVH composite), wherein the 2SiV content is 30 wt %.

1 g of SiPVH thus obtained is dissolved in Chloroform (9.3 g) and stirred to obtain a spinning solution. This spinning solution is loaded into an electrospinning machine and electrospun to obtain fiber wadding under the following conditions.

Conditions of Electrospinning

Supply speed of spinning solution::0.2 ml/min, Voltage applied:17 kV, distance between nozzle and collector (filled with ethanol): about 20 cm, Nozzle: syringe:18 G As shown in FIG. 12, the fibers accumulated in ethanol at the collector are recovered from the collector (FIG. 12). Samples 1-4 were prepared from the fiber wadding recovered from the collectors and analyzed. Bulk density, compressibility and compression recovery were measured in accordance with JIS L 1097.

1) Diameter of Fibers

Diameters of fibers were measured using a laser microscope from eighteen points. It was found that while the diameter of each fiber thus measured significantly varied, the distribution range of diameter was about 10 μm~21 μm.

2) Bulk Density

Each of the samples 1-4 (average weight: 0.055 g) was placed in a glass cylinder having inner diameter of 22 mm. A circular glass cover having approximately the same diameter (weight: 1.148 g) was placed on the fiber wadding in the glass cylinder. Height of fiber wadding ($h_0$) in the glass cylinder having the cover placed thereon was measured. Bulk density of the fiber wadding was calculated based on the volume of the fiber wadding thus measured and its weight. (shown in FIG. 13 (A)).

The result was that although varied significantly among the samples, bulk density of each sample was as follows: Sample 1: 0.015 g/cm$^3$, Sample 2: 0.014 g/cm$^3$, Sample 3: 0.018 g/cm$^3$ Sample 4: 0.021 g/cm$^3$ (average: 0.017 g/cm$^3$).

3) Compressibility and Compression Recovery

Figure 13C:
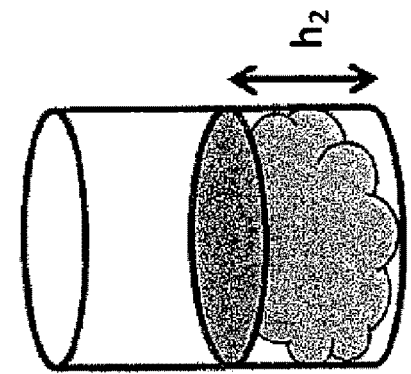
FIG. 13 (A) shows an explanatory view of measurement of bulk density of the fiber wadding prepared in Example 3.
Figure 13B:
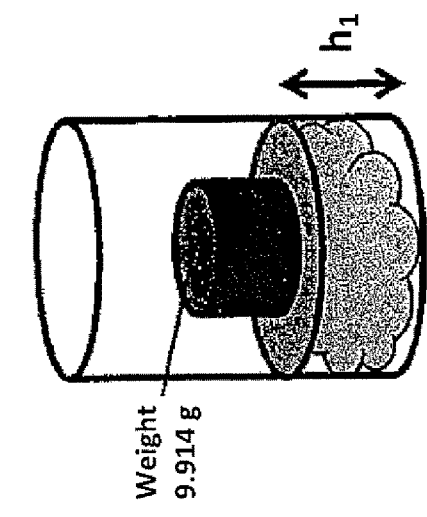

As shown in FIG. 13(B), a weight of 9.914 g is placed on the glass cover placed in the glass cylinder. After 30 minutes passed, height of the fiber wadding ($h_f$) in the glass cylinder in that state was measured. From the change before and after placing the weight on the cover, compressibility of fiber wadding was calculated using following formula.

$$\text{Compressibility}(\%)=(h_0-h_f)/h_0\times100$$

Compressibility of the fiber wadding of samples 1-4 thus measured was: Sample 1: 45.56%, Sample 2: 34.90%, Sample 3: 29.01%, Sample 4: 37.80% (Average 36.82%).

Figure 13A:
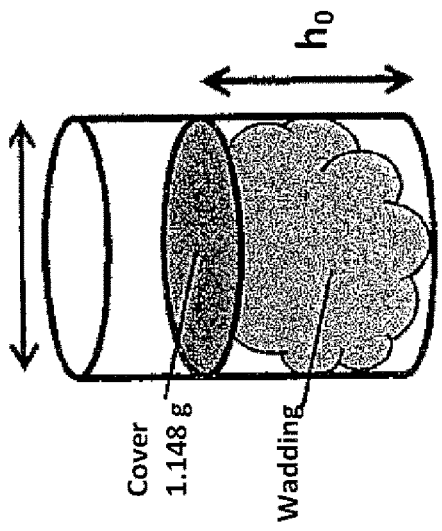

Next, as shown in FIG. 13 (C), the weight is removed from the glass cover. After 30 minutes, height of the fiber wadding ($h_2$) in the glass cylinder in that state was measured. From the change before and after placing the weight on the cover and removing the weight from the cover, compression recovery of the fiber wadding was calculated using following formula:

Compression recovery(%)=$(h_2-h_1)/(h_0-h_1)\times 100$

Compression recovery of fiber wadding of Sample 1-4 was as follows: Sample 1: 58.47%, Sample 2: 44.02%, Sample 3: 56.14%, Sample 4: 57.20% (Average 53.96%).

JIS L1097 Test Method—1982 (confirmed in 2008)

Japanese Industrial Standards (JIS) publishes standard method. L 1097 for the testing of synthetic fiber wadding in 1982, which is confirmed in 2008. The test is conducted in a room with class 2 standard temperature and humidity (temperature 20±2° C., relative humidity 65±2%,) according to JIS Z 8703 (standard condition of test room).

Preparation of Samples

Take pieces of wadding out of an unpackaged product and leave each pieces in the room for more than 8 hours. Then, randomly pick samples for testing. The test samples of 20×20 cm size are piled up such that mass weight thereof becomes about 40 g. Pieces of test samples necessary for conducting the test are left in that state for about one hour.

The tests could include testing for color, specific volume (bulk), compressibility (compression, recovery), fiber length, and quality.

Test method

Specific Volume (Bulk)

Specific volume is measured by measuring the weight of the test samples prepared as described above. A thick plate (a flat plate of 20×20 cm in size and 0.5 g/cm$^2$) is placed on a test piece and a weight A (2 Kg) is placed thereon for 30 minutes. Then, the weight A is removed and the test sample is left for 30 minutes in that state. This procedure is repeated three times. After the weight A is removed and left for thirty minutes in that state, the heights of the sample at four corners are measured and an average height is obtained. Specific volume is calculated using the following formula. The test should be performed with three samples and an average of the three samples is obtained.

Specific volume($cm^3/g$)=$(20\times 20\times h_0/10)/W$ wherein $h_0$ is an average value of the height at four corners of the test sample (mm), and W is the weight of the test sample (g). The specific volume (cm$^3$/g) can be readily converted in bulk density (g/cm$^3$).

Compression Elasticity (Compressibility, Compression Recovery)

Compression elasticity is measured by measuring height at four corners of a test piece described above. A mass B (4 Kg) is placed thereon for 30 minutes. The heights at four corners are measured. Thereafter, the weigh B is removed, and the test sample is left for 3 minutes. The heights at four corners are measured. Average values of those are obtained. Compressibility and compression recovery are calculated in accordance with following formula. The test is conducted for three samples, and an average of the three samples is obtained.

Compressibility(%)=$((h_0-h_1)/h_0)\times 100$

Compression recovery(%)=$(h_2-h_1)/(h_0-h_1)\times 100$ $h_0$: average height at four corners before placing weight B thereon (mm).

$h_1$: average height at four corners with weight B placed thereon (mm).

$h_2$: average height at four corners after weight B is removed (mm).

While the above description is of the preferred embodiments of the present invention, it would be appreciated by one skilled in the art that the invention may be modified, altered, or varied without deviating from the scope and fair meaning of the following claims.

What is claimed is:

1. A fiber wadding for filling bone defects, comprising:
a plurality of biodegradable fibers produced by using an electrospinning apparatus having a collector filled with ethanol, wherein electrospun fibers emitted from a nozzle of the electrospinning apparatus enter into the ethanol of the collector, and the fiber sink in the ethanol and are deposited in the collector,
wherein the plurality of biodegradable fibers are entangled with each other to form a flocculent three dimensional structure having a bulk density from about 0.01 g/cm$^3$ to about 0.1 g/cm$^3$, as measured in accordance with JIS L 1097,
wherein the plurality of biodegradable fibers comprise a biodegradable resin and a Si-releasable calcium compound.

2. The fiber wadding according to claim 1, wherein the Si-releasable calcium compound comprises calcium phosphate.

3. The fiber wadding according to claim 1, wherein outside diameter of the biodegradable fibers is from about 0.05 µm to about 30 µm.

4. The fiber wadding according to claim 1, wherein the biodegradable resin comprises poly(lactic acid) or a copolymer thereof.

5. The fiber wadding according to claim 1, wherein compressibility of the fiber wadding as measured in accordance with JIS L 1097 is from about 10% to about 55%.

6. The fiber wadding according to claim 1, wherein compressibility of the fiber wadding as measured in accordance with JIS L 1097 is from about 20% to about 55%.

7. The fiber wadding according to claim 1, wherein compressibility of the fiber wadding as measured in accordance with JIS L 1097 is from about 29% to about 55%.

8. The fiber wadding according to claim 1, wherein compression recovery of the fiber wadding as measured in accordance with JIS L 1097 is from about 5% to about 76%.

9. The fiber wadding according to claim 1, wherein compression recovery of the fiber wadding as measured in accordance with JIS L 1097 is from about 7% to about 76%.

10. The fiber wadding according to claim 1, wherein compression recovery of the fiber wadding as measured in accordance with JIS L 1097 is from about 44% to about 58%.

11. A fiber wadding for filling bone defects, comprising:
a plurality of biodegradable fibers produced by using an electrospinning apparatus having a collector filled with ethanol, wherein electrospun fibers emitted from a nozzle of the electrospinning apparatus enter into the ethanol of the collector, and the fibers sink in the ethanol and are deposited in the collector,
wherein the plurality of biodegradable fibers comprise a biodegradable resin and a bone formation element, and
wherein the plurality of biodegradable fibers are entangled with each other to form a flocculent three dimensional structure having a bulk density from about 0.01 g/cm$^3$ to about 0.1 g/cm$^3$, compressibility from about 10% to about 55%, and compression recovery from about 5% to about 76%, as measured in accordance with JIS L 1097.

12. The fiber wadding according to claim 11, wherein the bone formation element comprises a Si-releasable calcium compound.

\* \* \* \* \*